Figure 1:
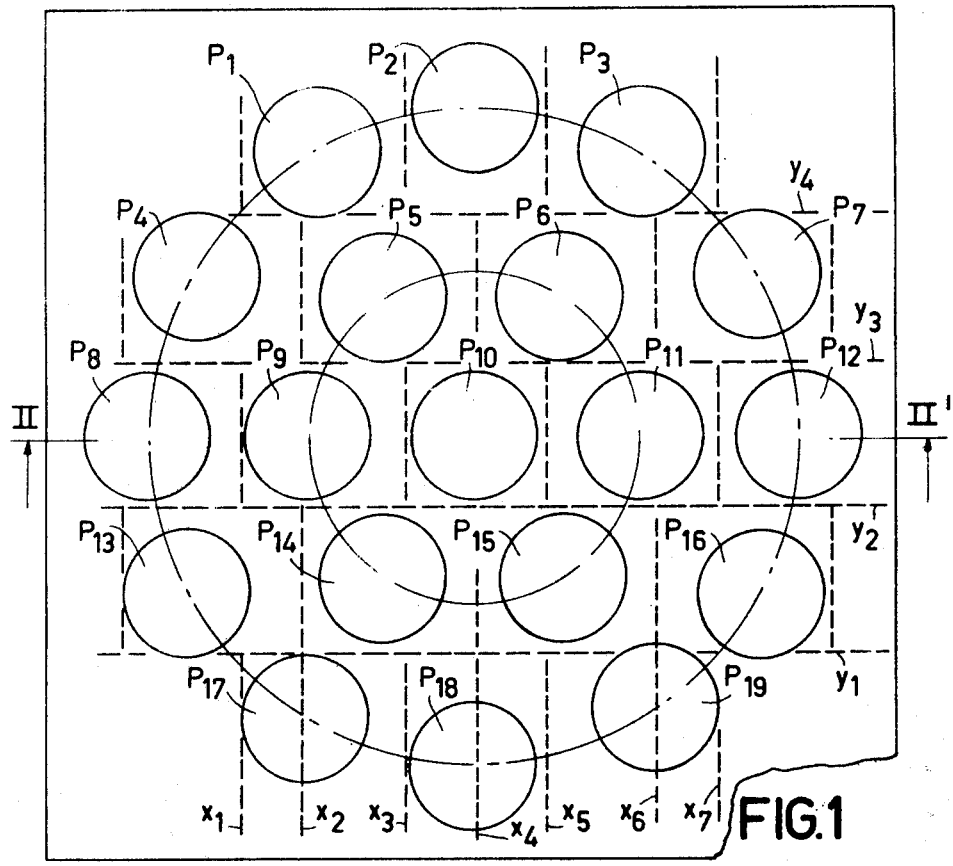

United States Patent [19]

Lelong et al.

[11] 4,424,447
[45] Jan. 3, 1984

[54] GAMMA CAMERA COMPRISING AN ELECTRONIC DEVICE FOR THE CORRECTION OF LINEARITY ERRORS

[75] Inventors: Pierre H. Lelong, Gentilly; Jean H. Ott, Ste Genevieve, both of France

[73] Assignee: U.S. Philips Corporation, New York, N.Y.

[21] Appl. No.: 248,914

[22] Filed: Mar. 30, 1981

[30] Foreign Application Priority Data

Apr. 4, 1980 [FR] France ............... 80 07762

[51] Int. Cl.³ .................................. G01T 1/20
[52] U.S. Cl. ................................... 250/363 S
[58] Field of Search .......................... 250/363 S

[56] References Cited

U.S. PATENT DOCUMENTS

| | | | |
|---|---|---|---|
| 3,011,057 | 11/1961 | Anger | 250/363 S |
| 3,745,345 | 7/1973 | Muehllehner | 250/363 S |
| 4,179,607 | 12/1979 | Lange et al. | 250/363 S |
| 4,223,388 | 9/1980 | Nishikawa et al. | 250/363 S X |
| 4,281,382 | 7/1981 | Knoll et al. | 250/363 S X |
| 4,298,944 | 11/1981 | Stoub et al. | 250/363 S X |
| 4,316,257 | 2/1982 | Del Medico et al. | 250/363 S X |

Primary Examiner—Davis L. Willis
Attorney, Agent, or Firm—Paul R. Miller

[57] ABSTRACT

The invention relates to a gamma camera for forming the image of a radiation distribution, comprising a scintillation crystal, several photomultipliers which are arranged according to a regular array opposite a surface of the scintillation crystal, the photosensitive surface of each photomultiplier facing the scintillation crystal, each photomultiplier being connected to arithmetic circuits which calculate the coordinates of the scintillations on the basis of the signals applied thereto by the photomultipliers, the gamma camera furthermore comprising an electrical circuit for correcting the calculated coordinates, the corrections being determined by the distance between the scintillation and the center of the photomultiplier tube situated nearest to the scintillation.

23 Claims, 7 Drawing Figures

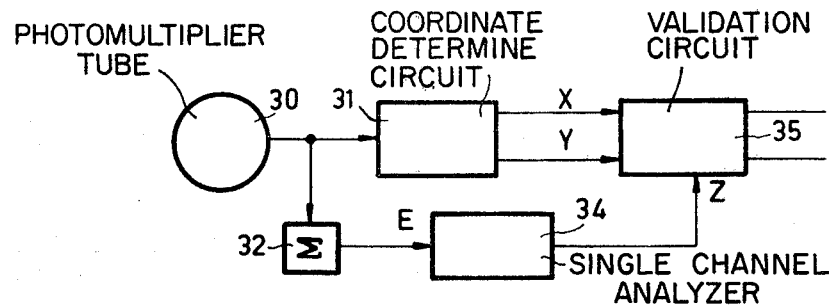
FIG. 3
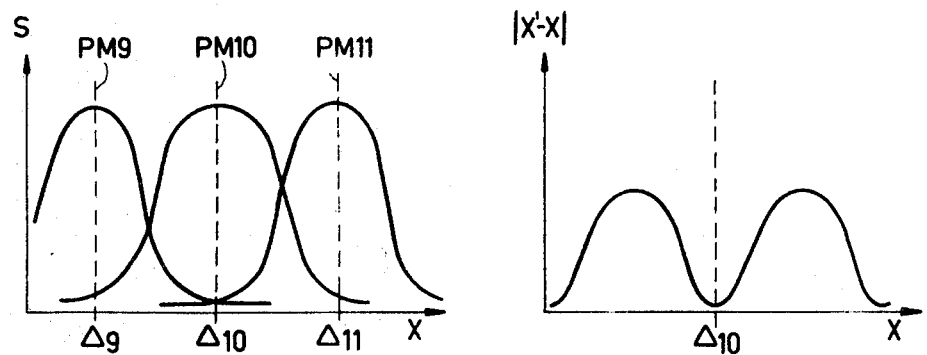
FIG. 4
FIG. 5
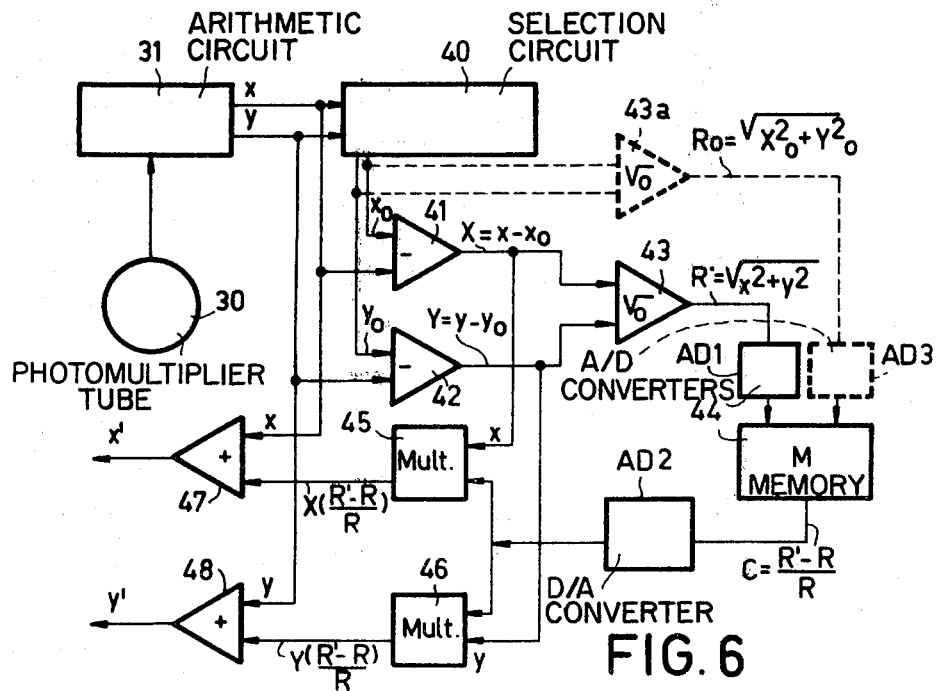
FIG. 6

GAMMA CAMERA COMPRISING AN ELECTRONIC DEVICE FOR THE CORRECTION OF LINEARITY ERRORS

The invention relates to a gamma camera for forming an image of a radiation distribution in a body comprising a scintillation crystal for generating local scintillations by gamma radiation intercepted by the crystal, several photomultiplier tubes which are arranged in a regular array so that their photosensitive surface is opposite the surface of the scintillation crystal in order to produce output signals in response to the local scintillations, an arithmetic circuit for determining, on the basis of the output signals to be applied thereto, the coordinates of the local scintillations, and a correction device for correcting the coordinates determined.

Such gamma cameras (of the Anger-type) are known, for example, from U.S. Pat. No. 3,011,057. These cameras are widely used in the field of nuclear medicine in order to obtain images of the radioactivity distribution in a human body after injection of a radioactive contrast medium whose life is generally short and which emits gamma rays, for example, a soluble salt of $Tc_m{}^{99}$ or $In_m{}^{113}$. The gamma radiation distribution emitted by this medium can be studied on the basis of the images obtained in order to derive a diagnosis.

The gamma radiation is filtered by a collimator so that only the gamma rays are admitted which are incident on the scintillation crystal at a given angle with respect to the surface of the scintillation crystal (usually 90°). These gamma rays then penetrate into the scintillation crystal and with a comparatively high probability they produce a scintillation in a point which is thus in a spatial relationship with the relevant point of the human body wherefrom the gamma radiation is emitted.

The light produced by the scintillation is intercepted by an array of photomultiplier tubes which is arranged in a predetermined position with respect to the scintillation crystal, with the photomultipliers generating output signals in reaction to the light. The output signals are applied to an arithmetic circuit in order to determine the spatial coordinates of the scintillations from the output signals.

Numerous improvements have been made to the gamma cameras as regards the intensity of the output signals of the photomultipliers as well as regards the choice of an energy window for the elimination of parasitic radiation (cosmic rays, Compton effect . . . ).

However, the spatial resolution of the Anger-type gamma cameras is limited by a shortcoming which is inherent of the use of photomultiplier tubes and which results in spatial non-linearity. Even when the scintillation crystal intercepts gamma radiation in which the spatial distribution density is uniform, the image obtained on the display screen of the cathode ray tube displaying the calculated points will exhibit a non-uniform spatial distribution. The distribution density of the calculated points is higher in the parts of the screen which correspond to the centers and their direct vicinity of the photomultiplier tubes.

Actually, the images of the scintillations are shifted nearer to the centers of the various photomultiplier tubes. So-called "hot spots" or "concentration areas" are formed.

Improvements which are intended to prevent the occurrence of such concentration areas have already been proposed in the form of an electronic device for the correction of the spatial coordinates of the scintillations; the correction method consists in that for each point of the entire image correction factors are measured and stored in a memory or are calculated by interpolation. Subsequently, these correction factors are used for the correction of each set of calculated coordinates. An improvement of this kind is described, for example, in U.S. Pat. No. 3,745,345.

A correction method of this kind is theoretically exact, but requires a comparatively large arithmetic and storage capacity, which means that an expensive arithmetic device and a readily accessible memory are required.

The invention also has for its object to prevent the occurrence of concentration areas around the centers of the various photomultiplier tubes by means of an electronic device whose construction, however, requires less storage capacity and which is also comparatively simple.

To this end, the gamma camera in accordance with the invention is characterized in that the correction device comprises means for determining the center of a photomultiplier tube which is situated nearest to the local scintillation, means for determining a distance signal which is a measure of the distance between the local scintillation and the center, and means for determining corrected coordinates of the local scintillation on the basis of the distance signal determined.

It has been established that for each photomultiplier tube the occurrence of concentration areas exhibits a given symmetry with respect to the center of the tube. Consequently, the correction factors can be stored in a memory having a comparatively small capacity. It has been found that it suffices to determine discrete correction factors for a single radius of the circle which defines the image field of a photomultiplier tube. For a suitable approximation of the analog correction function, a number of, for example, 32 factors already suffices.

A further embodiment of a gamma camera in accordance with the invention is characterized in that means for determining the center of a photomultiplier tube which is situated nearest to a local scintillation comprise a circuit for generating signals which are a measure of positions of separating lines which separate scintillation zones situated directly opposite the photomultiplier tubes, comparator circuits for comparing the coordinate signals with the separating line signals, logic circuits for deriving a tube number indication from the comparator output signals, and switching means controlled by the logic circuits in order to connect two outputs to a circuit for generating signals which are a measure of the coordinates of the centre of the photomultiplier tube indicated by the tube number indication.

The invention will be described in detail hereinafter with reference to the accompanying drawing.

Figure 2:
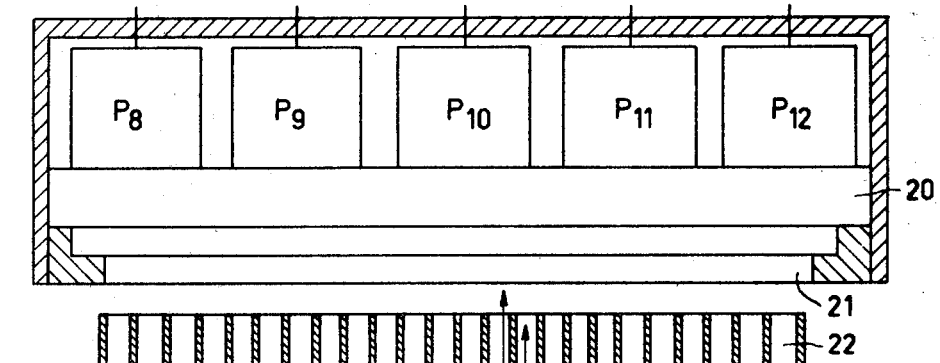
Figure 2:
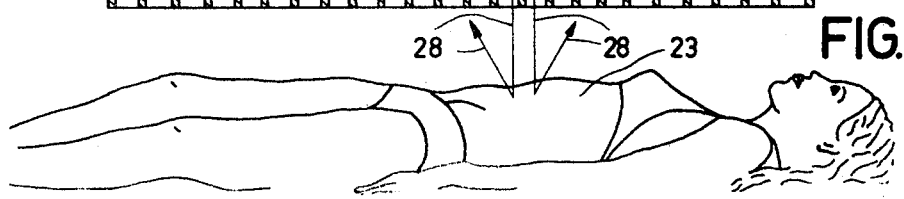
Figure 7:
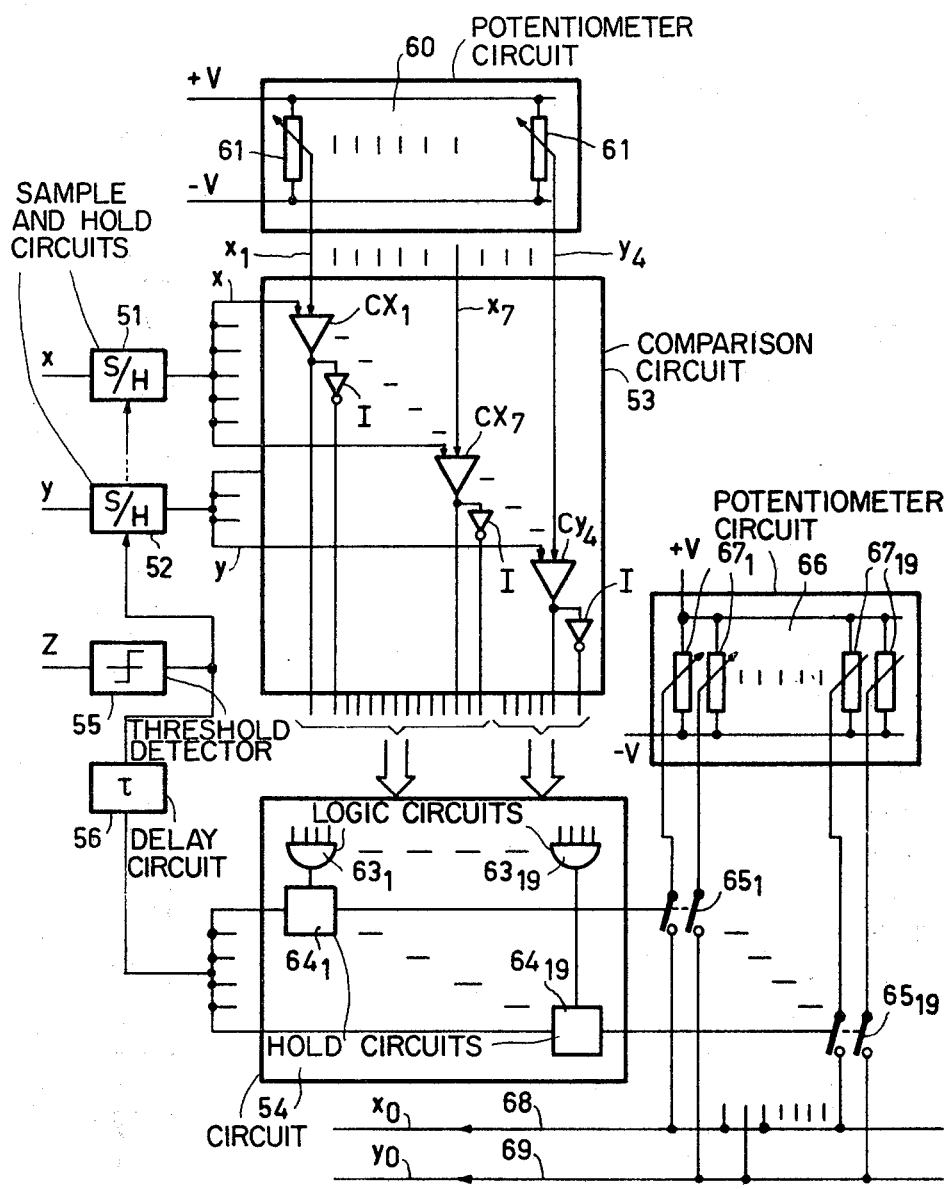

FIG. 1 diagrammatically shows the arrangement of the photomultiplier tubes in an Anger-type gamma camera, FIG. 2 is a sectional view of the gamma camera, FIG. 3 is a block diagram of a gamma camera for processing the output signals supplied by the tubes in known manner, FIG. 4 is a graph showing the variation of the output signal of some photomultiplier tubes in dependence of the position of a location scintillation with respect to the centres of the tubes, FIG. 5 shows the error in the calculation of the coordinates in dependence of the position with respect to the centre of a photomultiplier tube, FIG. 6 is a block diagram of a gamma camera comprising an electronic device for correcting the coordinates in accordance with the invention, and FIG. 7 is a more detailed representation of a selection device for the coordinates of the photomultiplier tube which is situated nearest to a local scintillation.

FIG. 1 shows the arrangement of the photomultiplier tubes which is generally used in Anger-type cameras in which nineteen photomultiplier tubes are arranged in a hexagonal array of the type 3-4-5-4-3 so that the photocathodes of the tubes are situated opposite the crystal and that the image fields of the photomultiplier tubes overlap.

FIG. 2 is a sectional view taken along the axis II—II' in FIG. 1. The five photomultiplier tubes are denoted by the references P8, P9, P10, P11 and P12 and are arranged along the center line of the described conventional array. These tubes are arranged on a light guide 20 which is usually formed by two parts, notably a disk of PERSPEX and a PYREX window. The light guide 20 is arranged opposite a disk-shaped scintillation crystal 21 which is made of thallium-activated sodium iodide. A collimator 22 filters the gamma rays 28 emitted by a body 23 being examined so that only the gamma rays which are incident on the scintillation crystal 21 at a given angle are transmitted. The transmitted rays are usually directed perpendicularly to the surface of the scintillation crystal.

A gamma radiation source, for example, a human body 23 injected with a solution of a radioactive salt, emits radiation in all directions with only the radiation which is directed perpendicularly to the surface of the scintillation crystal 21 penetrating into the crystal. Very likely local scintillations will then occur whose locations is in a spatial relationship with a given point in the body 23 wherefrom the gamma radiation originates. Photomultiplier tubes intercept this light and produce output signals which are integrated in order to obtain a measure for the intercepted energy and which are applied to an arithmetic circuit in order to determine the co-ordinates of the local scintillations.

The block diagram shown in FIG. 3 illustrates the processing of the output signals produced by the photomultipliers P1, . . . P19 in known gamma cameras. The output signals of the array of photomultiplier tubes 30 are applied to a device 31 for determining coordinates of local scintillations. The device 31 may be of the type as described, for example, in U.S. Pat. No. 3,011,057. Two signals concerning the calculated coordinates x and y become available on the output thereof. The output signals supplied by the array 30 are applied to an integrator 32 which supplies a signal having the energy E which is applied to a single-channel analyser 34 having a wide energy window. The analyser 34 supplies a validity signal Z if the value of the signal having the energy E is within the energy window of the analyser 34. The coordinate signals x and y are applied to a validation circuit 35 which comprises, for example, a display device such as a cathode ray tube, the signal Z being used to produce the electron beam.

Already known are gamma cameras which comprise a device for correcting the coordinates x and y. The correction device may be an optical device, for example, formed by elements which diffuse the light and which are comparatively opaque and are arranged between the scintillation crystal and the photomultiplier tubes, mainly in front of the tubes in the central part of the camera. Optical elements of this kind are described in French Patent Specificiation No. 2,168,250. The correction device may also be an electronic device. A first example in this respect is described in French Patent Specification No. 2,219,424 in which an electronic correction is performed on the output signals supplied by the photomultiplier tubes. A further example of an electronic device is described in U.S. Pat. No. 3,745,345 in which a comparatively complex arithmetic circuit and a large memory are used in which correction factors for the coordinates calculated for each point are stored or are calculated by interpolation.

The invention relates to a gamma camera comprising an electronic correction device and is based on a symmetry phenomenon established during the point-wise measurement of correction factors. When the scintillation crystal is irradiated by a point-shaped gamma radiation source which extends along a line which passes through the centers of photomultiplier tubes P9, P10 and P11, for the output signal of the tube P10 a curve is obtained as shown in FIG. 4 in which the x-axis denotes the position of the source with respect to the axis of the photomultiplier tube P10 while the axis perpendicular thereto represents the intensity s of the output signal. FIG. 4 also shows the output signals of the photomultiplier tubes P9 and P11. FIG. 5 simularly shows the spatial non-linearity of an Anger-type camera. The x-axis represents the position of the point-shaped source with respect to the axis of a photomultiplier tube, for example, P10, while the axis perpendicular thereto represents the absolute error between the calculated position X' and the actual position X. This error is substantially zero in the centre of the photomultipler tubes and increases to a maximum value as a function of the distance between the source and the center and subsequently decreases to a minimum value for the same distance between the centers of two adjacent photomultiplier tubes. The image produced by a uniform gamma radiation distribution has a higher light distribution density in the central regions of the photomultiplier tubes. These higher light concentrations are often referred to as hot spots and notably disturb a diagnosis, because the concentrations may simulate or distort accumulation points of the radioactive contrast medium. The curve shown in FIG. 5 is symmetrical with respect to the central axis ($\Delta$) of the photomultiplier tube. It has been found that this symmetry line is maintained, regardless of the direction wherefrom the line intersects the axis of the tube. It will be understood therefrom that any error occurring in the coordinates is dependent only on its distance from the center of a photomultiplier tube, and not on its angular position.

Thus, the invention consists in the conversion of the cartesian coordinates (x, y) of the position of the local scintillation with respect to a center of the (nearest) photomultiplier tube into polar coordinates (R, $\theta$), followed by a correction in dependence of the modulus of R on the basis of correction factors which may be identical for all tubes and which are stored in a memory having a small capacity (for example, in a memory having a capacity of 32 words of four bits each), and finally the formation of corrected cartesian coordinates.

FIG. 6 shows the block diagram of the device for correcting cartesian coordinates in accordance with the invention. The arithmetic circuit 31 (see FIG. 3) determines the coordinates of a local scintillation in the form of two signals x and y from the set of output signals supplied by the array 30 of photomultiplier tubes. On the basis of the signals x and y, a circuit 40 selects the coordinates of the photomultiplier tube situated nearest to the coordinates (x, y) and supplies two coordinate signals ($x_o$, $y_o$) which are a measure of the coordinates of the center of the tube. The coordinate signals $x_o$ and $y_o$ are applied to the negative terminals of two operational (differential) amplifiers 41 and 42, the positive terminals thereof receiving the coordinate signals x and y. The two differential amplifiers 41 and 42 supply new signals X and Y, respectively, in a new system of coordinates whose origin is the center of the nearest photomultiplier tube. The two signals X and Y are applied to the two inputs of an analog arithmetic circuit 43 which comprises analog multiplier circuits (for example, AD 530 or 531, μA 795) and whose output supplies a distance signal R of the sum of the squares of the applied signals X and Y. The distance signal R of the circuit 43 is a measure of the modulus of a vector whose components are the two input signals X and Y. The signal R is applied to an analog/digital converter AD1, the outputs of which are connected to a memory device 44. The memory 44, for example, a memory type SN 74187 or a programmable read-only memory type SN 74186, there are stored correction factors C which are presented on the output of the memory 44 and which are actually selected on the basis of the output signal R of the circuit 44. The memory 44 contains, for example, 32 words of four bits each. The calculated modulus of the signals X and Y is denoted by R and the corrected modulus is denoted by R'. On the output of the memory 44 a correction factor C is then presented which actually represents the relative error of the modulus R. The correction factor C corresponds to the value:

$$C = \frac{R' - R}{R}$$

The digital value of C is converted into analog form by a digital/analog converter DA2. Multipliers 45 and 46 correct the signals X and Y by multiplying the signals by the analog correction factor C. The outputs of adders 47 and 48, the inputs of which receive coordinate signals x and y determined by the arithmetic circuit 31 and also the relevant correction values X.C and Y.C, present the corrected coordinates x' and y', which can be mathematically expressed as follows:

$$\begin{cases} x' = x + X\left(\frac{R' - R}{R}\right) = x_o + (x - x_o) \cdot \frac{R'}{R} \\ y' = y + Y\left(\frac{R' - R}{R}\right) = y_o + (y - y_o) \cdot \frac{R'}{R} \end{cases}$$

FIG. 7 is a more detailed representation of the selection circuit 40 of FIG. 6 for the selection of the photomultiplier tube which is situated nearest to a local scintillation. The selection circuit 40 comprises two sample and hold circuits 51 and 52 whereto the calculated coordinate signals x and y are applied. The coordinate signals presented on the output of these two circuits 51 and 52 are applied to a comparison device 53 in which the coordinate signals x and y are compared with separating line signals $x_i$ and $y_i$ which are a measure of the coordinates of a given number of straight lines which define the arrangement of the photomultiplier tubes shown in FIG. 1. The separating line signals $x_i$ and $y_i$ are permanently applied to the comparison device 53. The various separating lines separate the scintillation zones situated directly opposite the photomultiplier tubes. The separating lines are denoted by broken lines in the FIG. 1.

For the determination of the coordinates of the center of the photomultiplier tube which is situated nearest to a local scintillation it is only necessary to establish for which indices i and j the coordinate signals satisfy $x_i < x < x_{i+1}$ and $y_j < y < y_{j+1}$. One fixed combination of indices i and j is associated with each photomultiplier tube. For example, the indices i=2; j=1 are associated with the photomultiplier tube P14. The separating line signals $x_i$ and $y_j$ are generated in a potentiometer circuit 60 whereto two voltages +V and −V are applied. The circuit 60 comprises a number of (i+j) potentiometers 61, only two of which are shown in the figure and whose setting corresponds to the position of the axes shown in FIG. 1. The comparison circuit 53 comprises a number of comparators $CX_1, \ldots CX_7$ and $CY_1 \ldots CY_4$, whereto the signals $x_1, \ldots x_7$ and $y_1 \ldots y_4$, respectively, are applied. The coordinate signals x and y are applied to the comparators $CX_i$ and $CY_j$, respectively.

If $x > x_1$, the output of the comparator $CX_1$ carries a "high" potential (for example, 4 volts), referred to as $a_1 = 1$; if not, the output of the comparator $CX_1$ carries a "low" potential (for example, 0.2 volts), referred to as $a_1 = 0$. Each comparator output is connected to an inverting gate i so that, in addition to the logic signals $a_i$ and $b_j$, also the inverse values $\bar{a}_i$ and $\bar{b}_j$ thereof are available. From the logic signals $a_i$, $\bar{a}_i$, $b_j$ and $\bar{b}_j$, a tube number indication can be derived by means of logic circuits $63_1 \ldots 63_{19}$ to indicate which photomultiplier tube $P_1 \ldots P_{19}$ is situated nearest to the local scintillation. For example, for $P_9$, the expressions $x_1 \leq x \leq x_2$ and $y_2 \leq y \leq y_3$ or $x_2 \leq x \leq x_3$ and $y_2 \leq y \leq y_3$ are correct. These expressions can be rewritten as $x_1 \leq x \leq x_3$ n $y_2 \leq y \leq y_3$. This logic expression is satisfied if the output signals of the comparators $CX_1$, $CX_3$, $CY_2$ and $CY_3$ satisfy the equation $a_1 \cdot \bar{a}_3 \cdot b_2 \cdot \bar{b}_3 = 1$. When the signals $a_1$, $\bar{a}_3$, $b_2$ and $\bar{b}_3$ are applied to the AND-gate $63_9$, the output thereof will carry a high potential signal if a local scintillation has indeed occurred nearest to the center of the photomultiplier tube $P_9$. Therefore, for each photomultiplier tube $P_1 \ldots P_{19}$ there is provided one logic AND-gate $63_1 \ldots 63_{19}$ with a maximum of four inputs, the output of each AND-gate $63_1 \ldots 63_{19}$ supplying an unambiguous tube number indication whether or not the associated photomultiplier tube $P_1 \ldots P_{19}$ has its center situated nearest to the relevant local scintillation. The output levels (high or low) are stored by bistable hold circuits $64_1 \ldots 64_{19}$ until the position of a next scintillation is determined. The outputs of the hold circuits $64_1 \ldots 64_{19}$ control switching means $65_1 \ldots 65_{19}$. Only the switch $65_i$ associated with the hold circuit $64_i$ which has received a high output level (i.e. tube number indication i) from the AND-gate $63_i$ is closed. The double switch $65_i$ may be a relay or an electronic switch (transistor) and connects a potentiometer circuit 66 to two outputs 68 and 69 on which there are presented the coordinate signals $x_o$ and $y_o$ which are associated with the center of the photomultiplier tube $P_i$ situated nearest to the local scintillation. To this end, for each photomultiplier tube $P_i$ the potentiometer circuit 66 comprises two potentiometers $67_i$ (2×19 in this example, only four of which are shown in the Figure), each potentiometer supplying a signal which corresponds to the $x_1$ and the $y_1$ coordinate, respectively, of the tube i.

The signal Z locks and unlocks the circuits 51, 52 and 54 of the selection circuit 40. The signal Z behaves as an enable signal when the amount of energy of the light generated by a local scintillation is sufficient. To this end, the signal Z is applied to an upper and lower threshold detector 55. In other words, an enable signal is applied to the circuits 51, 52 and 54 of the selection device 40 only if the level of the signal Z is within a predetermined window. If the level of the signal Z is below the lower threshold, the threshold detector 55 will not present an enable signal on its output. For the operation of such a detector, reference is made, for example, to the article "Applications du double détecteur de seuil, à fenêtre adjustable", by G. GEHRIAG and J. M. ZULAUF, published in "Microélectronique", Apr. 1976. Preferably, a delay line 56 is included in order to compensate for the different delay times of the signals in the device.

In the embodiment of a gamma camera in accordance with the invention described thus far, the correction factors C are identical for all photomultiplier tubes, so that a very simple correction device is obtained.

In a further embodiment of a gamma camera in accordance with the invention, the correction factors C are identical for the tubes associated with the same ring of the regular array, which means that the same correction factors are used, for all photomultiplier tubes (P5, P6, P9, P11, P15, P16) which are situated at the same distance from the center (of the tube P10) of the gamma camera. Such an embodiment has the advantage that the precision is higher, but the block diagram shown in FIG. 6 then requires some modifications. The modification (denoted by broken lines in FIG. 6) implies that the signals $x_o$ and $y_o$ are applied to an analog arithmetic circuit 43' which is identical to the circuit 43 of FIG. 6. The output of the arithmetic circuit supplies a signal $R_o = \sqrt{x_o^2 + y_o^2}$ which is applied to an analog/digital converter AD3. The output of the converter AD3 is connected to inputs of a memory 44 whereto the output of the analog/digital converter AD1 is also connected. This circuit enables the selection of a group of correction factors C which depend on the distance $R_o$ between the relevant photomultiplier tube $P_i$ and the center of the tube P10. The memory 44, however, should have a memory capacity which corresponds to the number of groups of correction factors.

It is alternatively possible to store the correction factors $C = R'/R$ instead of the correction factors $$C = \frac{R^1 - R}{R};$$

in that case the signals $x_o$ and $y_o$ should be applied to the amplifiers 47 and 48, respectively, instead of the coordinate signals x and y. The equations $$x' = x_o + C \cdot X = x_o + \frac{R'}{R} \cdot (x - x_o) \text{ and}$$

$$y' = y_o + C \cdot Y = y_o + \frac{R'}{R} \cdot (y - y_o)$$

are then again satisfied in agreement with the already described formules.

It will be clear that within the scope of the invention various modifications will be possible for those skilled in the art.

What is claimed is:

1. A gamma camera for forming an image of a radiation distribution in the body, comprising a scintillation crystal for generating local scintillations by gamma radiation intercepted by the crystal, several photomultiplier tubes which are arranged in a regular array so that their photosensitive surface is opposite the surface of the scintillation crystal in order to produce output signals in response to the local scintillations, an arithmetic circuit for determining, on the basis of the output signals to be applied thereto, the coordinates of the local scintillations, and a correction device for correcting the coordinates determined, characterized in that, the correction device comprises means for determining the center of a photomultiplier tube which is situated nearest to the local scintillation, means for determining a distance signal which is a measure of the distance between the local scintillation and said center, and means for determining corrected coordinates of the local scintillation on the basis of the distance signal determined.

2. A gamma camera as claimed in claim 1, characterized in that correction factors are identical for all photomultiplier tubes.

3. A gamma camera as claimed in claim 2, characterized in that means for determining the center of a photomultiplier tube which is situated nearest to a local scintillation comprise a circuit for generating signals which are a measure of positions of separating lines which separate scintillation zones situated directly opposite the photomultiplier tubes, comparator circuits for comparing the coordinate signals with the separating line signals, logic circuits for deriving a tube number indication from the comparator output signals, and switching means controlled by the logic circuits in order to connect two outputs to a circuit for generating signals which are a measure of the coordinates of the center of the photomultiplier tube indicated by the tube number indication.

4. A gamma camera as claimed in claim 3, characterized in that the logic circuits comprise an AND-gate and bistable hold circuit per photomultiplier tube, the inputs of the AND-gate being connected to outputs of the comparator circuit, and the output of the AND-gate being connected to the input of the hold circuit.

5. A gamma camera as claimed in claim 2, characterized in that the means for determining the distance signal comprise differential amplifiers for determining a difference signal between the coordinate signals and the signals indicating the center of a photomultiplier tube, multiplier circuits which are connected to outputs of the differential amplifiers in order to determine the square of the difference signals, and a circuit which is connected to the output of the multiplier circuit in order to determine a distance signal which is proportional to the square root of the sum of the squares of the difference signals.

6. A gamma camera as claimed in claim 2, characterized in that the means for determining corrected coordinates of the local scintillation on the basis of the distance signal comprise a memory for the storage of correction factors which can be addressed by means of the distance signal, multiplier circuits for multiplying difference signals representative of the difference between the coordinates of the center of the photomultiplier tubes and the coordinates of a local scintillation by the correction factor, and an adder circuit for adding the difference signals multiplied by the correction factor to the coordinate signals.

7. A gamma camera as claimed in claim 6, characterized in that the memory is a read only memory (ROM), between the circuit for determining the distance signal and the memory there being connected an analog/digital converter while a digital/analog converter is connected between the memory and the multiplier circuits for multiplying the difference signals by the correction factor.

8. A gamma camera as claimed in claim 6, characterized in that the correction device also comprises multiplier circuits for determining the squares of the signals indicating the center of the photomultiplier tube and a circuit for determining the square root of the sum of the squares, the output of said circuit being connected to an input of the memory.

9. A gamma camera as claimed in claim 1, in which the regular array is formed by points of intersection of a number of concentric circles with radii which extend from the center of the circles and which all enclose the same angle two by two, characterized in that correction factors for the photomultiplier tubes whose centers are situated on the same circle are identical.

10. A gamma camera as claimed in claim 9, characterized in that means for determining the center of a photomultiplier tube which is situated nearest to a local scintillation comprise a circuit for generating signals which are a measure of positions of separating lines which separate scintillation zones situated directly opposite the photomultiplier tubes, comparator circuits for comparing the coordinate signals with the separating line signals, logic circuits for deriving a tube number indication from the comparator output signals, and switching means controlled by the logic circuits in order to connect two outputs to a circuit for generating signals which are measure of the coordinates of the center of the photomultiplier tube indicated by the tube number indication.

11. A gamma camera as claimed in claim 10, characterized in that the means for determining the distance signal comprises differential amplifiers for determining a difference signal between the coordinate signals and the signals indicating the center of a photomultiplier tube, multiplier circuits which are connected to outputs of differential amplifiers in order to determine the square of the difference signals and a circuit which is connected to the output of the multiplier circuit in order to determine a distance signal which is proportional to the square root of the sum of the squares of the difference signals.

12. A gamma camera as claimed in claim 10, characterized in that the logic circuits comprise an AND-gate and a bistable hold circuit per photomultiplier tube, the inputs of the AND-gate being connected to outputs of the comparator circuit, the output of the AND-gate being connected to the input of the hold circuit.

13. A gamma camera as claimed in claim 12, characterized in that the means for determining the distance signal comprise differential amplifiers for determining a difference signal between the coordinate signals and the signals indicating the center of a photomultiplier tube, multiplier circuits which are connected to outputs of the differential amplifiers in order to determine the square of the difference signals, and a circuit which is connected to the output of the multiplier circuit in order to determine a distance signal which is proportional to the square root of the sum of the squares of the difference signals.

14. A gamma camera as claimed in claim 9, characterized in that the means for determining corrected coordinates of the local scintillation on the basis of the distance signal comprise a memory for the storage of correction factors which can be addressed by means of the distance signal, multiplier circuits for multiplying difference signals representative of the difference between the coordinates of the center of the photomultiplier tubes and the coordinates of a local scintillation by the correction factor, and an adder circuit for adding the difference signals multiplied by the correction factor to the coordinate signals.

15. A gamma camera as claimed in claim 14, characterized in that the memory is a read only memory (ROM), between the circuit for determining the distance signal and the memory there being connected an analog/digital converter while a digital/analog converter is connected between the memory and the multiplier circuits for multiplying the difference signals by the correction factor.

16. A gamma camera as claimed in claim 14, characterized in that the correction device also comprises multiplier circuits for determining the squares of the signals indicating the center of the photomultiplier tube and a circuit for determining the square root of the sum of the squares, the output of said circuit being connected to an input of the memory.

17. A gamma camera as claimed in claim 9, characterized in that the means for determining the distance signal comprise differential amplifiers for determining a difference signal between the coordinate signals and the signals indicating the center of a photomultiplier tube, multiplier circuits which are connected to outputs of the differential amplifiers in order to determine the square of the difference signals, and a circuit which is connected to the output of the multiplier circuit in order to determine a distance signal which is proportional to the square root of the sum of the squares of the difference signals.

18. A gamma camera as claimed in claim 1, characterized in that means for determining the center of a photomultiplier tube which is situated nearest to a local scintillation comprise a circuit for generating signals which are a measure of positions of separating lines which separate scintillation zones situated directly opposite the photomultiplier tubes, comparator circuits for comparing the coordinate signals with the separating line signals, logic circuits for deriving a tube number indication from the comparator output signals, and switching means controlled by the logic circuits in order to connect two outputs of a circuit for generating signals which are a measure of the coordinates of the center of the photomultiplier tube indicated by the tube number indication.

19. A gamma camera as claimed in claim 18, characterized in that the logic circuits comprise an AND-gate and a bistable hold circuit per photomultiplier tube, the inputs of the AND-gate being connected to outputs of the comparator circuit, and the output of the AND-gate being connected to the input of the hold circuit.

20. A gamma camera as claimed in claim 1, characterized in that the means for determining the distance signal comprise differential amplifiers for determining a difference signal between the coordinate signals and the signals indicating the center of a photomultiplier tube, multiplier circuits which are connected to outputs of the differential amplifiers in order to determine the square of the difference signals, and a circuit which is connected to the output of the multiplier circuit in order to determine a distance signal which is proportional to the square root of the sum of the squares of the difference signals.

21. A gamma camera as claimed in claim 1, characterized in that the means for determining corrected coordinates of the local scintillation on the basis of the distance signal comprise a memory for the storage of correction factors which can be addressed by means of the distance signal, multiplier circuits for multiplying difference signals representative of the difference between the coordinates of the center of the photomultiplier tubes and the coordinates of a local scintillation by the correction factor, and an adder circuit for adding the difference signals multiplied by the correction factor to the coordinate signals.

22. A gamma camera as claimed in claim 21, characterized in that the memory is a read only memory (ROM), between the circuit for determining the distance signal and the memory there being connected an analog/digital converter while a digital/analog converter is connected between the memory and the multiplier circuits for multiplying the difference signals by the correction factor.

23. A gamma camera as claimed in claim 21, characterized in that the correction device also comprises multiplier circuits for determining the squares of the signals indicating the center of a photomultiplier tube and a circuit for determining the square root of the sum of the squares, the output of said circuit being connected to an input of the memory.

* * * * *